United States Patent [19]

König et al.

[11] 4,098,779

[45] Jul. 4, 1978

[54] PROCESS FOR THE PURIFICATION AND MANUFACTURE OF SECRETIN

[75] Inventors: Wolfgang König, Hofheim am Taunus; Rolf Geiger, Frankfurt am Main; Rainer Obermeier, Hattersheim; Volker Teetz, Hofheim am Taunus, all of Fed. Rep. of Germany

[73] Assignee: Hoechst Aktiengesellschaft, Frankfurt am Main, Fed. Rep. of Germany

[21] Appl. No.: 785,181

[22] Filed: Apr. 6, 1977

[30] Foreign Application Priority Data

Apr. 8, 1976 [DE] Fed. Rep. of Germany ....... 2615229

[51] Int. Cl.² .......................................... C07C 103/52
[52] U.S. Cl. ............................................ 260/112.5 R
[58] Field of Search .............................. 260/112.5 R

[56] References Cited

PUBLICATIONS

G. Jäger, et al., Chem. Ber. 107, 215–231 (1974).
Wunsch, et al., Chem. Ber. 105, 2515–2522 (1972).
V. Mutt, et al., J. Chromatog. 24 (1966), 205–207.
E. Nyström, et al., J. Chromatog. 24, (1966), pp. 208–212.
B. Almé, et al., J. Chromatography 59, (1971), pp. 45–52.

*Primary Examiner*—Delbert R. Phillips
*Attorney, Agent, or Firm*—Curtis, Morris & Safford

[57] ABSTRACT

A process for the purification of secretin by chromatography on an alkylated dextran gel is disclosed, as is a method of its manufacture appropriate for preparing larger amounts of secretin.

4 Claims, No Drawings

PROCESS FOR THE PURIFICATION AND MANUFACTURE OF SECRETIN

Secretin, a hormone from the duodenum, is a heptacosipeptide of the formula

H-His-Ser-Asp-Gly-Thr-Phe-Thr-Ser-Glu-Leu-Ser-
Arg-Leu-Arg-Asp-Ser-Ala-Arg-Leu-Gln-Arg-
Leu-Leu-Gln-Gly-Leu-Val-NH$_2$.

It stimulates the bicarbonate production of the pancreas and is used clinically to examine the function of the pancreas.

Hitherto, secretin has been purified by countercurrent distribution (J. Am. Chem. Soc. 89, 6753 (1967)) and ion exchange chromatography on SP-Sephadex C 25 (Chem. Ber. 105 (1972), page 2515). In the case of expensive countercurrent distribution, the secretin-containing samples are subsequently stirred with an acidic exchanger ("algenic acid") and suction filtered. The secretin absorbed during this process is eluted with 0.2 N HCL and the hydrochloric acid is exchanged for acetic acid on a weakly basic exchanger. Thus, after countercurrent distribution, two steps of ion exchange chromatography are still necessary for working up.

When purifying by means of ion exchange chromatography on SP-Sephadex C 25, secretin acetate, which is obtained from crude secretin by treating it with a weakly basic ion exchanger (in acetate form), is eluted with ammonium carbonate buffers of increasing molarity and with particular pH values. Elution takes a relatively long time and the resulting eluates contain, in addition to secretin, ammonium carbonate that must be converted into ammonium acetate by acidification with acetic acid and must be removed by freeze-drying several times.

However, since secretin in aqueous solutions steadily loses its biological activity, only small amounts of highly active secretin can be obtained with the two previously-known, time-consuming methods of purification for, with larger amounts, the residence time becomes too long and thus also the loss of activity too great.

It has now surprisingly been found that secretin as the hydrochloride or hydrobromide can be purified by chromatography on an alkylated dextran gel if elution is effected with water or very dilute hydrochloric acid or hydrobromic acid. Preferably, 0.001 - 0.005 N hydrochloric acid or hydrobromic acid is used for elution since the biological activity of secretin does not decrease as rapidly in these solutions as in pure water.

The advantage of this method is that only a single, simple purification operation is necessary and the secretin can be obtained free of salt by freeze-drying once. The acidic elution agent can also be buffered with amino acids, such as, for example, cysteine, alanine or glycine. Even in these buffered solvents, the biological activity of the secretin is maintained better than in pure water. The secretin thus obtained is, however, contaminated by the amino acid which has been added but this may even possibly be desired for some forms of preparation.

Secretin has already been prepared by various methods (J. Amer. Chem. Soc. 89 (1967), page 6753; J. Amer. Chem. Soc. 90 (1968), page 4711; Chem. Ber. 105 (1972), page 2508; Chem. Ber. 107 (1974), page 215). However, these known methods are not well-suited to preparing relatively large amounts of secretin since, e.g., insufficient solubility of fragments slows down the reaction speed in the case of peptide coupling.

Therefore, the subject of the invention is also a process for the preparation of secretin by condensing Z—Thr(Bu')—Ser(Bu')—Glu(OBu')—Leu-Ser(Bu')-
Arg—Leu—OH   (I)

with

H-Arg-Asp(OBu')-Ser(Bu')-Ala-Arg-Leu-Gln-Arg-
Leu-Leu-Gln-Gly-Leu-Val-NH$_2$   (II)

catalytic hydrogenation of the peptide obtained

Z-Thr(Bu')-Ser(Bu')-Glu(OBu')-Leu-Ser(Bu')-Arg-
Leu-Arg-Asp(OBu')-Ser(Bu')-Ala-Arg-Leu-Gln-
Arg-Leu-Leu- Gln-Gly-Leu-Val-NH$_2$   (III)

with a palladium catalyst and subsequent condensation of the peptide obtained

H-Thr(Bu')-Ser(Bu')-Glu(OBu')-Leu-Ser(Bu')-Arg-
Leu-Arg-Asp(OBu')-Ser(Bu')-Ala-Arg-Leu-Gln-
Arg-Leu-Leu-Gln-Gly-Leu-Val-NH$_2$   (IV)

with

Boc-His-Ser(Bu')-Asp(OBu')-Gly-Thr(Bu')-Phe-OH   (V)

and splitting off the protective groups with trifluoroacetic acid, which process is characterized in that, in the condensation operations the peptide fragments I and V are pre-activated in a mixture of dimethylformamide and dimethylacetamide with 3-hydroxy-4-oxo-3,4-dihydro-1,2,3-benzotriazine and dicyclohexylcarbodiimide, the presence of pyridine hydrobromide being necessary in the case of I. The peptide III obtained from I with II is purified by treatment in methanol. The catalytic hydrogenation of III is effected in 80 to 90% strength aqueous trifluoroethanol. The peptide IV is pre-dissolved in a dimethylformamide/dimethylacetamide mixture in the case of the condensation of IV with V, and the protective groups are split off in the presence of 5 to 20% strength 2 – 6 N HCl or HBr and/or cysteine hydrochloride. The secretin hydrochloride thus obtained is purified according to the invention as above.

When linking I with II, the dicyclohexylcarbodiimide/1-hydroxybenzotriazole (DCC/HOBt) method has hitherto been used (Chem. Ber. 107 (1974), page 215). However, the fact that the carboxyl component is extremely difficult to dissolve presents considerable difficulties. For a 7.7 mMol batch, 400 ml of dimethylformamide (DMF) are required as the solvent. As a result of the high degree of dilution, the reaction speed is greatly reduced and a long reaction time (2 days) is required.

It has now surprisingly been found that the carboxyl component I that is difficult to dissolve dissolves well in the presence of pyridine-hydrobromide and 3-hydroxy-4-oxo-3,4-dihydro-benzotriazine (HOOBt) in a mixture of DMF and dimethylacetamide (DMA). If one of the components is omitted the solubility is reduced. This behavior is ideal for pre-activation of the heptapeptide, which is difficult to dissolve, by means of DCC/HOOBt. The pyridine hydrobromide is used to protonate the free guanidine group of the arginine. Thus, only 50 ml of DMF and 50 ml of DMA are necessary to dissolve 10 mMol of carboxyl component I. Pre-activation takes 2 hours. The amino component II (10 mMol) is likewise dissolved in a mixture of 50 ml of DMF and 50 ml of DMA. After a coupling time of two hours, working-up is effected. The total solvent consumption is therefore 200 ml/10 mMol and the total reaction time is 4 hours.

In the final coupling too, viz. the linking of V with IV to form Boc-His-Ser(Bu')-Asp(OBu')-Gly-Thr(Bu')-Phe-Thr(Bu')-Ser(Bu')-Glu(OBu')-Leu-Ser(Bu')-Arg-Leu-Arg-Asp(OBu')-Ser(Bu')-Ala-Arg-Leu-Gln-Arg-Leu-Leu-Gln-Gly-Leu-Val-NH$_2$, the pre-activation of the carboxyl component with DCC/HOOBt is superior to the one-pot process with DCC/HOBt (Chem. Ber. 107 (1974) page 215), a mixture of DMF and DMA again being used as the solvent for the amino component. In this case the reaction time is reduced from 36 to 6 hours.

The peptide III obtained by condensing I with II has been purified hitherto by boiling out with ethyl acetate (Chem. Ber. 107 (1974), page 215) and by dissolving and re-precipitating from methanol/ethyl acetate (Chem. Ber. 105 (1972) page 2508). Understandably, these purification operations have no great purifying effect on the starting substances that are not readily soluble. It has surprisingly been found that the material can be boiled out with methanol and a greater purifying effect is obtained, this being in contrast to the literature last-mentioned (Chem. Ber. 105, (1972) page 2508) according to which the peptide is soluble in methanol.

The catalytic hydrogenation of III to form IV has hitherto been effected in a mixture of methanol and DMA (143 ml/g, cf. Chem. Ber. 107, 215) or in 80% strength acetic acid (269 ml/g, Chem. Ber. 105, 2508). 80 – 90% strength 2,2,2-trifluoroethanol (11 ml/g) has now proved to be a particularly suitable solvent for catalytic hydrogenation. This solvent has the advantage over acetic acid that acetylation cannot take place in the mixture methanol/DMA. The product III purified with methanol was practically insoluble in the mixture methanol/DMA.

After catalytic hydrogenation, the resulting 5HBr H-Thr(Bu')-Ser(Bu')-Glu(OBu')-Leu-Ser(Bu')-Arg-Leu-Arg-Asp(OBu')-Ser(Bu')-Ala-Arg-Leu-Gln-Arg-Leu-Leu-Gln-Gly-Leu-Val-NH$_2$ (IV) can be purified satisfactorily by boiling out with methanol again, although the product is described as soluble in methanol in Chem. Ber. 105 (1972), page 2508.

The protected secretin thus produced can be treated as usual with trifluoroacetic acid, the protective groups of the tert.-butyl type being split off.

However, splitting off the protective groups in trifluoroacetic acid, to which 5 – 20% 2 – 6N aqueous hydrochloric acid and/or cysteine hydrochloride is added, has proved more advantageous. With this process a more highly active crude secretin is obtained that can be readily purified according to the purification process of the invention by chromatography on an alkylated dextran gel.

Secretin is used as a diagnostic agent for investigating the excretory functions of the pancreas and as a therapeutic agent for *ulcus duodeni*.

The following Examples illustrate the invention.

EXAMPLE

Z-Thr-(Bu')-Ser(Bu')-Gln(OBu')-Leu-Ser(Bu')-Arg-Leu-Arg-Asp(OBu')-Ser(Bu')-Alg-Arg-Leu-Gln-Arg-Leu-Leu-Gln-Gly-Leu-Val-NH$_2$ 8.4 g of dicyclohexylcarbodiimide are added to a solution of 12 g of Z-Thr(Bu')-Ser(Bu')-Glu(OBu')-Leu-Ser(Bu')-Arg-Leu-OH.2 H$_2$O, 1.6 g of pyridine hydrobromide and 1.63 g of 3-hydroxy-4-oxo-3,4-dihydro-1,2,3-benzotriazine in a mixture of 50 ml of dimethylformamide and 50 ml of dimethylacetamide and the whole is stirred for two hours at room temperature. Meanwhile, 18.8 g of H-Arg-Asp(OBu')-Ser(Bu')-Ala-Arg-Leu-Gln-Arg-Leu-Leu-Gln-Gly-Leu-Val-NH$_2$.4 HBr and 5.2 ml of N-ethylmorpholine are dissolved in a mixture of 50 ml of dimethylformamide and 50 ml of dimethylacetamide. The pre-activating batch is filtered into this solution. The whole is then stirred for a further two hours at room temperature and stirred into 3 liters of ethyl acetate. The resulting precipitate is suction filtered, boiled up once with ethyl acetate, and suction filtered again. For further purification, the whole is boiled up once with 200 ml of methanol and suction filtered. The whole is then stirred once again with ethyl acetate, boiled up, cooled, suction filtered and dried.

Yield. 23.1g, m.p.:262°–265° C [α]$_D^{20}$ = −22.4° (c = 1, in 80% acetic acid).

Z-Thr-(Bu')-Ser(Bu')-Glu(OBu')-Leu-Ser(Bu')-Arg-Leu-Arg-Asp(OBu')-Ser(Bu')-Ala-Arg-Leu-Gln-Arg-Leu-Leu-Gln-Gly-Leu-Val-NH$_2$.5 HBr 6 g of Z-Thr(Bu')-Ser(Bu')-Glu(OBu')-Leu-Ser(Bu')-Arg-Leu-Arg-Asp(OBu')-Ser(Bu')-Ala-Arg-Leu-Gln-Arg-Leu-Leu-Gln-Gly-Leu-Val-NH$_2$ and 300 mg of pyridine hydrochloride are dissolved in 70 ml of 80% trifluoroethanol. A little Pd/carbon catalyst is added and hydrogen is passed through. When hydrogenation is complete (no CO$_2$ in the exhaust gas) the catalyst is suction filtered and the trifluoroethanol is distilled off. The residue is triturated with ethyl acetate and suction filtered. For further purification boiling-up is effected with methanol. The whole is allowed to come to room temperature and is suction filtered. Boiling-up is then effected once again with ethyl acetate followed by cooling and suction filtering.

Yield 4.58 g, [α]$_D^{20}$ = −26.1° (c = 1, in 80% acetic acid).

Boc-His-Ser(Bu')-Asp(OBu')-Gly-Thr(Bu')-Phe-Thr(Bu')-Ser(Bu')Glu(OBu')-Leu-Ser(Bu')-Arg-Leu-Arg-Asp(OBu')-Ser(Bu')-Ala-Arg-Leu-Gln-Arg-Leu-Leu-Gln-Gly-Leu-Val-NH$_2$ 2.87 g of DCCI are added at 0° C to a solution of 4.24 g of Boc-His-Ser (Bu')-Asp(OBu')-Gly-Thr(Bu')-Phe-OH and 709 mg of 3-hydroxy-4-oxo-3,4-dihydro-1,2,3-benzotriazine in 17 ml of dimethylacetamide. Stirring is effected for one hour at 0° C and for one hour at room temperature. Meanwhile, 13.7 g of H-Thr(Bu')-Ser(-Bu')-Glu(OBu')-Leu-Ser(Bu')-Arg-Leu-Arg-Asp(OBu')-Ser(Bu')-Ala-Arg-Leu-Gln-Arg-Leu-Gln-Gly-Leu-Val-NH$_2$.5HBr are dissolved in a mixture of 87 ml of dimethylformamide and 87 ml of dimethylacetamide to form a gelatinous mass. 1.13 ml of N-ethylmorpholine are added to this gelatinous solution, dilution is effected with 22 ml of dimethylacetamide and the pre-activating batch is suction filtered into this mixture. Stirring is then effected for two hours at room temperature. Meanwhile another pre-activating batch is prepared as above which is again filtered into the reaction batch. The whole is stirred for a further two hours at room temperature and the gelatinous solution is then stirred with 1740 ml of hot ethyl acetate. The whole is allowed to cool to room temperature and the precipitate is suction filtered. The precipitate is boiled up once again with ethyl acetate, suction filtered and dried. Yield 17 g.

Crude secretin and secretin purification (a) 1.5 g of protected secretin and 150 mg of cysteine hydrochloride are dissolved in a mixture of 15 ml of trifluoroacetic acid and 1.5 ml of 4 N HCl. The whole is allowed to stand for 30 minutes at room temperature, is concentrated, dissolved in water and the solution is freeze-dried. Yield 1.69 g. 1.69 g of crude secretin are dissolved in approximately 10 ml of 0.001 n cys. HCl solution and chromatographed on a Sephadex LH 20 column (200 × 4 cm). Elution is effected with 0.001 N cys. HCl solution. Fractions of 300 drops are collected. The good secretin fractions are contained in the descending branch of the first peak (approximately 32nd – 37th fraction). The secretin - containing fractions are combined and freeze-dried. Yield approx. 400 mg. In the following fractions a further 80 mg (approx.) of slightly contaminated secretin can be obtained. According to amino acid analysis the main fraction of 400 mg had a peptide content of 65% and a biological activity of 2600 U/mg; this corresponds to an activity of 4000 U/mg peptide base. Yield calculated on protected secretin: 22%. Apart from salts and water, the secretin thus isolated contains approximately a further 5% of cysteine hydrochloride. Amino acid analysis: Asp (2.0), Thr (1.9), Ser (3.1), Glu (3.0), Gly (2.0), Ala (1.1), Cys (0.7), Val (1.1), Leu (6.0), Phe (1.0), His (1.0), Arg (3.9).

(b) 1.5 g of protected secretin are dissolved in a mixture of 15 ml of trifluoroacetic acid and 1.5 ml of 4 N HCl. The whole is allowed to stand for 30 minutes at room temperature, is concentrated, dissolved in water and the solution is freeze-dried. Yield 1.328 g. The 1.328 g of crude secretin obtained above are dissolved in approx. 10 ml of 0.005 N HCl and chromatographed on a Sephadex LH 20 column (200 × 4 cm). Elution is effected with 0.005 N HCl. Fractions of 300 drops are collected. The good secretin fractions are contained in the rising branch of the second peak (approx. 34th – 39th fraction). The fractions are combined and freeze-dried. Yield 419 mg. In the following fractions a further 296.5 mg of contaminated secretin can be obtained. According to amino acid analysis the main fraction of 419 mg had a peptide content of 70% and a biological activity of 2600 – 2700 U/mg. The amino acid analysis corresponds to that of test a) but does not contain cysteine.

We claim:

1. In a method for purifying synthetic secretin by chromatography, the improvement wherein secretin hydrochloride or secretin hydrobromide is chromatographed on Sephadex LH 20 and is eluted therefrom with water, dilute aqueous hydrochloric acid, or dilute aqueous hydrobromic acid.

2. A method as in claim 1 wherein said dilute aqueous hydrochloric or hydrobromic acid is buffered by the presence therein of an amino acid in an amount up to an amount equimolar with said acid.

3. In a process for the synthesis of secretin which comprises condensing

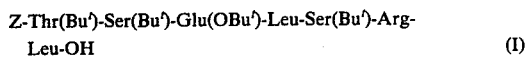

with

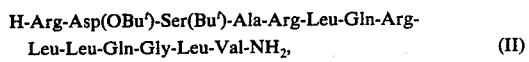

to obtain

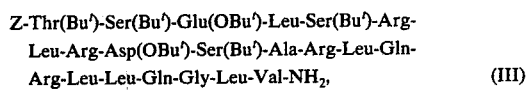

hydrogenating the peptide III in the presence of a palladium catalyst to obtain

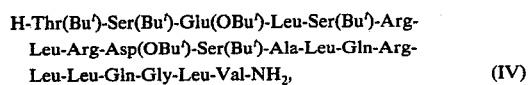

condensing the peptide IV with

and splitting off protective groups with trifluoroacetic acid, the improvement wherein peptide I is activated, prior to condensation with peptide II, with 3-hydroxy-4-oxo-3,4-dihydro-1,2,3-benzotriazine and dicyclohexylcarbodiimide in the presence of pyridine hydrobromide in a mixture of dimethylformamide and dimethylacetamide, peptide III is purified by treatment in methanol prior to catalytic hydrogenation, the catalytic hydrogenation of peptide III is effected in 80 to 90 percent aqueous trifluoroethanol, peptide IV is pre-dissolved in a mixture of dimethylformamide and dimethylacetate prior to condensation with peptide V, and peptide V is activated with 3-hydroxy-4-oxo-3,4-dihydro-1,2,3-benzotriazine and dicyclohexylcarbodiimide in a mixture of dimethylformamide and dimethylacetamide prior to condensation with peptide IV, and protective groups are split off with trifluoroacetic acid containing 5 to 20 percent of at least one member selected from the group consisting of 2N–6N hydrochloric acid hydrobromic acid, and cysteine hydrochloride.

4. A process as in claim 3 wherein the synthetic secretin obtained is purified by chromatographing it, as secretin hydrochloride or secretin hydrobromide, on Sephadex LH 20 and eluting it therefrom with water, dilute aqueous hydrochloric acid, or dilute aqueous hydrobromic acid.

* * * * *